US00PP14443P39

(12) United States Plant Patent
Hofmann

(10) Patent No.: US PP14,443 P3
(45) Date of Patent: Jan. 6, 2004

(54) IMPATIENS PLANT NAMED 'FISVISION'

(50) Latin Name: *Impatiens hawkeri×Impatiens auricoma*
Varietal Denomination: Fisvision

(75) Inventor: Birgit C. Hofmann, Bendorf (DE)

(73) Assignee: Fiorfis AG, Binningen (CH)

( * ) Notice: Subject to any disclaimer, the term of this patent is extended or adjusted under 35 U.S.C. 154(b) by 0 days.

(21) Appl. No.: 10/315,139

(22) Filed: Dec. 10, 2002

(65) Prior Publication Data

US 2003/0126663 P1 Jul. 3, 2003

(30) Foreign Application Priority Data

Dec. 28, 2001 (EP) ..... 2001-2157

(51) Int. Cl.[7] ..... A01H 5/00

(52) U.S. Cl. ..... Plt./317

(58) Field of Search ..... Plt./317, 318

*Primary Examiner*—Bruce R. Campell
*Assistant Examiner*—Susan B. McCormick
(74) *Attorney, Agent, or Firm*—Foley & Lardner

(57) ABSTRACT

A new and distinct cultivar of Impatiens plant named 'Fisvision', characterized by the combined features of light-yellow flower color RHS 8 B; medium-sized, cup-shaped, zygomorphic flowers with a short spur; uniform, medium green foliage, elliptically shaped; medium sized, low and wide, rounded, compact and well-branched plant habit; early flowering response; rich and continuously flowering; and strong resistance to heat and excellent tolerance of higher fertilizer levels/salt concentrations in the soil.

1 Drawing Sheet

Latin name of the genus and species of the plant claimed: A hybrid of the genus Impatiens (*Impatiens hawkeri×Impatiens auricoma*).
Variety denomination: 'Fisvision'.

BACKGROUND OF THE INVENTION

The present invention comprises a new and distinct cultivar of the genus Impatiens, hereinafter referred to by the cultivar name 'Fisvision'.

'Fisvision' is a product of a planned breeding program and originates from an inter-specific hybridization made by the inventor, Birgit Hofmann, in a controlled breeding program in Hillscheid, Germany, in 2000. The main objective of the breeding program was to introduce the novel trait of yellow flower color into the New Guinea Impatiens group.

The female parent was a New Guinea Impatiens hybrid seedling, no. K00-6158-1 (unpatented, proprietary plant material), characterized by round, white flowers, ever-flowering, deep green foliage for a white-flowered variety, elliptically shaped leaves, round and bushy plant habit, and medium growth vigor.

The male parent was an unnamed *Impatiens auricoma* plant of commercial origin (unpatented) with brilliant golden-yellow flowers, and a galeated corolla, roughly reminiscent of Aconitum flowers (buttercup family). The foliage of the male parent *Impatiens auricoma* plant is grass-green, narrow, and elliptically shaped. Its growth habit is vigorous and upright, and it has few branches initially.

Flowers of the female parent were pollinated by the above described *Impatiens auricoma* plant, which usually led to abscission of the ovaries before maturity of the seed capsules. Therefore, a few days after fertilization, the ovules with immature embryos were transferred into tissue culture. After a few months of development, 27 plantlets were successfully transferred into soil and grown in a greenhouse in the spring of 2001. These plants were found to be variable with respect to branching ability, the number of flowers developed, and presence or absence of leaf deformation. 'Fisvision' was discovered and selected by the inventor, as one flowering plant within the progeny in a greenhouse in Hillscheid, Germany, in August 2001.

The first act of vegetative reproduction of 'Fisvision' was accomplished when cuttings were taken from the initial selection in September, 2001, in a controlled environment in Hillscheid, Germany, by, or under the supervision of the inventor.

Horticultural examination of plants grown from cuttings of the plant initiated in the spring of 2002, in Hillscheid, Germany, has demonstrated that the combination of characteristics as herein disclosed for 'Fisvision' are firmly fixed and are retained through successive generations of asexual reproduction.

'Fisvision' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany under greenhouse conditions which approximate those generally used in commercial practice.

BRIEF SUMMARY OF THE INVENTION

The following traits have been repeatedly observed and are determined to be basic characteristics of "Fisvision", which in combination distinguish this impatiens as a new and distinct cultivar:

1. light-yellow flower color RHS 8 B;
2. medium-sized, cup-shaped, zygomorphic flowers with a short spur;
3. uniform, medium green foliage, elliptically shaped;

4. medium sized, low and wide, rounded, compact and well-branched plant habit;
5. early flowering response, rich and continuously flowering; and
6. strong resistance to heat and excellent tolerance of higher fertilizer levels/salt concentrations in soil for Impatiens.

As 'Fisvision' is an inter-specific hybrid, there is no very close variety for comparison purposes, other than the parental cultivars. In contrast to the female parent, seedling no K00-6158-1, 'Fisvision' has light yellow, instead of white, flower color, and the flower shape and size is different. Flowers of 'Fisvision' are smaller, about ⅔ thirds the size, and the flower shape is cup-shaped and zygomorphic, not flat or rounded. The shape, size and color of the leaves of both the female parent and the instant plant are similar. Lastly, 'Fisvision' has a similar plant shape to that of the female parent, but grows somewhat more slowly and stays more compact.

In comparison to the male parent, which has deep yellow, and nearly closed, galeated corolla, 'Fisvision' has a lighter yellow flower color and more open, cup-shaped corolla and a longer spur. It also has a deeper green foliage color, and plant habit is not erect, but bushy and relatively low, with distinctly less vigorous growth.

BRIEF DESCRIPTION OF THE DRAWINGS

The accompanying photographic drawing shows typical flower and foliage characteristics of 'Fisvision' with colors being as true as possible with illustrations of this type. The drawing shows a full side view of a potted 'Fisvision' plant at 3 months.

DETAILED BOTANICAL DESCRIPTION

In the following description, color references are made to The Royal Horticultural Society Colour Chart (1986 edition). The color values and description were determined indoors in May, 2002, from plants grown in Hillscheid, Federal Republic of Germany, under greenhouse conditions which approximate those generally used in commercial practice.

The plants were planted as rooted cuttings into 12 cm pots in early March and grown in temperatures of 18° C. at night, to 20–22° C. during the day. The measurements and most observations were made at the beginning of flowering, about 10 weeks later, from early to mid May.

Plant:

*Plant habit.*—Relatively compact, wide and low, uniformly mounded, and well-branched.

*Growth vigor.*—Medium, though weak at the outset of flowering.

*Height.*—16.5 cm.

*Width.*—29.5 cm.

*Internode length.*—15–20 mm.

*Stem color.*—Mainly green, RHS 147 B with brown infused, approximately RHS 166 B.

*Flowering response.*—9–10 weeks after planting of rooted cuttings.

*Flowering season.*—Almost year-round in a greenhouse, depending on light intensity.

*Propagation.*—Terminal shoot tips for cuttings.

*Rooting.*—Sufficiently rooted for transplanting after about 18–21 days at 22° C. temperature.

*Disease resistance.*—Resistance and/or susceptibility to diseases and pests was in no way different from other New Guinea Impatiens varieties.

*Heat tolerance.*—Better than most New Guinea Impatiens varieties.

Foliage:

*Arrangement.*—Primarily in whorls.

*Shape.*—Elliptic, with acute base and acute to acuminate tip, surface dull to slightly glossy, smooth or slightly rugose.

*Margin.*—Weakly serrated and ciliated.

*Leaf blade length.*—68 mm.

*Leaf blade width.*—31 mm.

*Upper surface leaf color.*—Medium green. Mature leaves: RHS 143 A. Young leaves: RHS 143 B. Veins: Light green, RHS 144 B. Variegation: None.

*Lower surface leaf color.*—RHS 143 C (both young and mature leaves). Veins: Light green with brownish pink infusion, approximately between RHS 144 B and 174 D.

*Petiole.*—Length: 0 to 2 mm, almost sessile. Color: Upper side brownish-pink, RHS 174 D, lower side between RHS 144 B and 174 D.

Inflorescence:

*Flower.*—Single flower on peduncles, arranged in whorls around the nodes, appear close to the surface of the foliage canopy.

*Number of flowers per node.*—6–8, in various stages of development, often more than one flower or bud per leaf axil.

*Corolla form.*—Single-type, 5 petals.

*Corolla shape.*—Zygomorphic, cup-shaped, the overlapping petals form a roughly triangular outline; the lower petals on each side are fused at the base.

*Corolla diameter.*—Average length: 41 mm. Average width: 35 mm. Average depth: 17 mm.

Petals:

*Upper petal.*—Nearly round, concave shape, with entire margin; 20 mm long, 22 mm wide, smooth, velvety texture.

*Lateral and lower petals.*—Heart-shaped, attenuate base, apex weakly lobed (marginate), margins of lower petals with a few irregular incisions, may appear slightly fringed aspect almost flat; average size 20 mm long, 18–20 mm wide; smooth, velvety texture.

*Color (general tonality from a distance of three meters).*—Light yellow. Main color of upper surface: RHS 8 B; may fade to RHS 8C or 8D, mainly during periods with very high light intensity.

*Color near petal bases.*—RHS 9 A.

*Color of inner markings.*—RHS 30 A (weak).

*Color of lower surface, main part.*—RHS 8 C, crest RHS 39 B.

*Calyx.*—Largest sepal yellow, between RHS 12 C and 12 D.

*Spur.*—Usually one spur per flower, occasionally two more, shorter ones emerge from the smaller sepals, 25 mm long, diameter 2–3 mm at the base, 0.5 to 1 mm near the tip, greenish yellow in color, RHS 154 A.

*Pedicel.*—Dull green, RHS 146 D; 30 mm length, 2 mm diameter.

*Buds.*—Ovoid to trigonus (three-corned), with crest (keel) and spur, light green RHS 144 C and yellow, RHS 8A to 8B, 17 mm long, 14 mm in diameter.

Reproductive organs:

Androecium:

*Stamens.*—5 in number, fused, upper surface color is mainly pale yellow, RHS 8C in color, about 7 mm in length.

*Anthers.*—Hooded, color about RHS 8 C.

*Pollen.*—Whitish-yellow, about RHS 8 D.

Gynoecium:

*Styles and stigmata.*—Five in number, very short, about RHS 4D in color.

*Ovary.*—5-celled, 7–9 mm long, surface color deep green, RHS 137 D.

Seed set and fertility: Although the organs appear normal, no seed set was observed (nor achieved after pollination), and pollen was found to be sterile when examined in laboratory.

I claim:

1. A new and distinct cultivar of Impatiens plant named 'Fisvision', as described and illustrated herein.

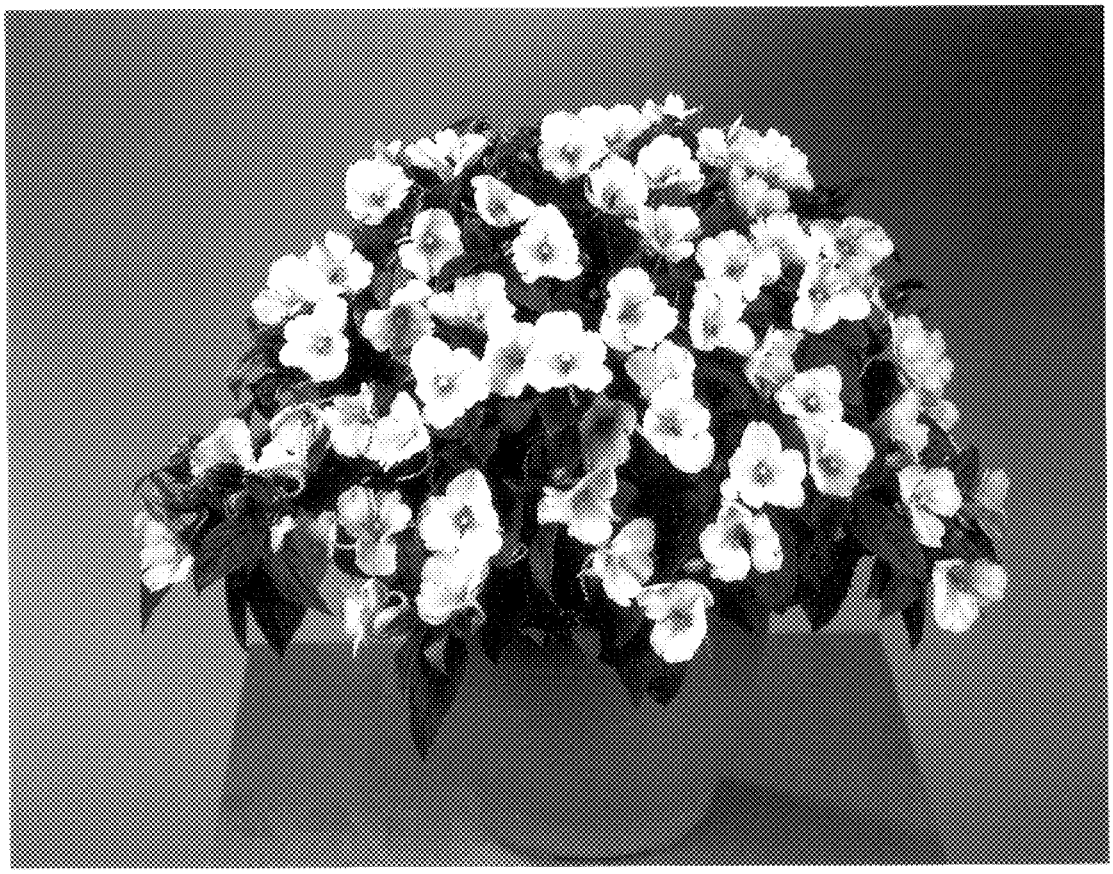

* * * * *